United States Patent
Vives et al.

(10) Patent No.: US 7,474,727 B2
(45) Date of Patent: Jan. 6, 2009

(54) DYNAMIC COMPUTED TOMOGRAPHY METHOD AND APPARATUS WITH TEMPORAL INTERPOLATION OF DATA IN PERFUSION STUDIES

(75) Inventors: Pau Montes Vives, Heidelberg (DE); Günter Lauritsch, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/581,016

(22) Filed: Oct. 12, 2006

(65) Prior Publication Data

US 2007/0092055 A1 Apr. 26, 2007

Related U.S. Application Data

(60) Provisional application No. 60/726,552, filed on Oct. 14, 2005.

(51) Int. Cl.
G01N 23/00 (2006.01)
(52) U.S. Cl. .............................................. 378/4; 378/8
(58) Field of Classification Search ............... 378/4–20, 378/901
See application file for complete search history.

(56) References Cited

U.S. PATENT DOCUMENTS

| 4,182,173 | A | * | 1/1980 | Papadofrangakis et al. ........ 73/861.27 |
| 4,672,651 | A | * | 6/1987 | Horiba et al. ............... 378/62 |
| 5,412,562 | A | * | 5/1995 | Nambu et al. ................ 378/10 |
| 5,544,215 | A | * | 8/1996 | Shroy et al. ............. 378/98.12 |
| 6,272,200 | B1 | * | 8/2001 | Pan et al. ....................... 378/15 |
| 6,620,103 | B1 | * | 9/2003 | Bruce et al. ................. 600/458 |
| 6,934,353 | B2 | * | 8/2005 | Wang et al. ..................... 378/8 |
| 7,042,975 | B2 | * | 5/2006 | Heuscher ....................... 378/8 |
| 7,153,268 | B2 | * | 12/2006 | Li et al. ..................... 600/455 |
| 2002/0196901 | A1 | * | 12/2002 | Inoue ......................... 378/154 |
| 2005/0169420 | A1 | * | 8/2005 | Edic et al. ...................... 378/4 |
| 2005/0251010 | A1 | * | 11/2005 | Mistretta et al. ............ 600/407 |

OTHER PUBLICATIONS

Danielsson, Iterative Techiniques for Projection and Back-projection, Department of Electrical Engineering, ISSN 1400-3902, Report No. LiTH-ISY-R-1960, Jun. 1997, p. 20.*

Grangeat et al., Theorectical framework for a dynamic cone-beam reconstruction algorithm based on a dynamic particle model, Physics in Medicine and Biology, 47, 2002, pp. 2611-2625.*

(Continued)

Primary Examiner—Edward J Glick
Assistant Examiner—Alexander H Taningco
(74) Attorney, Agent, or Firm—Schiff Hardin LLP

(57) ABSTRACT

In dynamic computed tomography a contrast agent is injected into a patient, and a region of interest where the contrast agent is flowing is then scanned with a computed tomography machine having a ray source and a ray detector. The ray source rotates. At a first rotational position of the ray source for a first rotation at a first time point a first image is obtained, and at the first rotational position for at least another rotation at a second time point a second image is obtained. For at least another rotational position of the ray source for the first rotation at a third time point a third image is obtained, and at the another rotational position for the another rotation at a fourth time point a fourth image is obtained. Time interpolations are performed and a reconstructed image is created.

14 Claims, 5 Drawing Sheets

OTHER PUBLICATIONS

Feldkamp L.A. et al—Practical Cone-Beam Algorithm—1984 Optical Society of America.

C. Kak Avinash et al Principles of Computerized Tomographic Imaging, IEEE Press, NY 1988 vol. 3.5, pp. 96-99.

M. Unser et al—B-Spline Signal Processing: Part II—Efficient Design and Applications—1993 IEEE February.

K. A. Miles et all Functional Computed Tomography, Publisher Isis Medical Media 1 Edition—Sep. 1997) ISBN: 189906639X, pp. 1-6.

Alan V. Oppenheim et al—Discrete-Time Signal Processing, Prentice Hall, Dec. 1998 2 Auflage, pp. 142-147 ISBN 0137549202.

Ernst Klotz et al—Perfusion Measurements of the Brain: Using Dynamic etc. European Journal of Radiology 30 (1999) 170-184.

Splines—A Perfect Fit for Signal and Image Processing Nov. 1999 M. Unser.

M. Grass et al 3D Cone-Beam CT Reconstruction for Circular Trajectories Phys. Med. Biol. 45 (2000) 329-347 Printed in the UK.

Henrik Turbell Cone-Beam Reconstruction Using Filtered Backprojection, Linköping Studies in Science and Technology—Dissertation No. 672, Feb. 2001, pp. 41-47.

S. Bonnet et al Time Delay Analysis in Online 4-D CT Fully 3D Image Reconstruction Meeting in Radiology and Nuclear Medicine, 2003.

Katsuyuki Taguchi Temporal Resolution and the Evaluation of Candidate Algorithms for Four Dimensional CT, Medical Physics, vol. 30, No. 4, pp. 640-650, Apr. 2003.

P. Montes et al Analysis of Time Resolution in Dynamic Computed Tomography for Perfusion Studies, IEEE Nuclear Science Symposium Conference Record, Rome, IT Oct. 16-22, 2004.

P. Montes et al Noise Reduction by Temporal Estimation in Perfusion Computed Tomography—Oct. 23-29, 2005.

Theoretical Framework for a Dynamic Cone-Beam Reconstruction Algorithm Based on a Dynamic Particle Model—Phys. Med. Biol. 47 (2002) 2611-2625.

Fractional Scan Algorithms for Low-Dose Perfusion CT Hsieh GE Medical Systems Med. Phys. 31 (5), May 2004 pp. 1254-1257.

* cited by examiner

DYNAMIC COMPUTED TOMOGRAPHY METHOD AND APPARATUS WITH TEMPORAL INTERPOLATION OF DATA IN PERFUSION STUDIES

RELATED APPLICATION

This application claims priority under 35 U.S.C. §119(e) from provisional U.S. application Ser. No. 60/726,552, filed Oct. 14, 2005 titled: DYNAMIC COMPUTED TOMOGRAPHY METHOD AND APPARATUS WITH TEMPORAL INTERPOLATION OF DATA IN PERFUSION STUDIES, incorporated herein by reference.

BACKGROUND

This disclosure concerns computed tomographic image reconstruction of dynamic objects. In particular, dynamic changes of the attenuation coefficients of the object (patient) are considered which typically occur when contrast agent is administered to the patient. In perfusion studies one is interested especially in such dynamic changes to compute perfusion properties of the tissue.

Nowadays perfusion computed tomography (CT) protocols typically acquire a complete set of projection data every second. Each set of projection data is interpreted as data of a static object and is processed by conventional reconstruction algorithms. The drawbacks of neglecting dynamic properties in the reconstruction step are manifold. The acquisition tie of a single set of projection data has to be short enough to justify the assumption of a static object during the acquisition. This restricts significantly the freedom in the sampling rate and enforces a sampling much denser than would be required by the frequency spectrum of the time attenuation curves (TAC) of the object.

Dynamic computed tomography (CT) has already found its way into clinical routine for visualization of functional processes. See K. Miles, P. Dawson, and M. Blomley, Functional Computed Tomography, Isis Medical Media, 1997; E. Klotz and M. König, "Perfusion Measurements of the Brain; Using Dynamic CT for the Quantitative Assessment of Cerebral Ischemia in Acute stroke," European Journal of Radiology, vol. 30, pp. 170-184, 1999. For example, for stroke patients the damage in the brain can be estimated by assessing parameters like perfusion and blood volume, time to peak, etc. Perfusion CT is a very fast, stable and accurate method easily available due to the widespread distribution of CT scanners.

In a typical perfusion CT protocol, after injection of a contrast agent, projection data are acquired continuously for a period of time of up to 40 seconds. A temporal sequence of slice images of a region of interest (ROI) is reconstructed. Typically one time frame is computed per scanner rotation with a rotation time of 1 second. The temporal evolution of the contrast enhancement (time-attenuation curves) due to the flow of contrast agent through the vessels and tissue is used to compute the functional parameters.

During the acquisition of the set of projections necessary to reconstruct an image, dynamic changes are ignored and each time frame is computed as in the static case. The introduction of large area detectors will allow the simultaneous scanning of an entire region of interest, thus enabling perfusion studies of an entire volume. The accompanying increase of clinical relevance will enforce quality improvements by incorporating dynamic properties into the reconstruction process Reconstruction from projection data of a dynamically changing object is a severe problem. Each projection is acquired at a different time representing the object in a different state. Thus the obtained data sets are inconsistent. If the dynamic changes in the object are fast relative to the rotational speed of the gantry, this leads to artifacts in the reconstructed frames around dynamically changing regions and errors in the reconstructed value of the attenuation coefficient within them.

Several approaches have been proposed in the literature to overcome the above-described problem. Taguchi suggested to use a generalized Parker-like weighting window to compensate the mismatch between projections at the endpoints of the scan. K. Taguchi, "Temporal resolution and the Evaluation of Candidate Algorithms for Four Dimensional CT," Medical Physics, vol. 30, no. 4, pp. 640-650, April 2003. See also A. C. Kak and M. Slaney, Principles of Computerized Tomographic Imaging. IEEE Press, 1988. A significant reduction of artifacts was observed. A more sophisticated method was proposed by Grangeat et al. where an estimate of data at any time instance was achieved by linear regression. P. Grangeat, A. Koenig, T. Rodet, and S. Bonnet, "Theoretical Framework for a Dynamic Cone-beam Reconstruction Algorithm based on a Dynamic Particle Model," Physics in Medicine and Biology, vol. 47, no. 15, August 2002.

SUMMARY

In a method for dynamic computed tomography wherein a contrast agent is injected into a patient, and a region of interest of the patient where the contrast agent is flowing is then scanned with a computed tomography machine, the computed tomography machine has a ray source and a ray detector. At least the ray source rotates relative to the region of interest of the patient. At a first rotational position of the ray source for a first rotation at a first time point a first image is obtained, and at said first rotational position for at least another rotation at a second time point a second image is obtained, the first and second images being different from one another in view of the flowing contrast agent. At least another rotational position of the ray source for the first rotation at a third time point a third image is obtained, and at the another rotational position for the another rotation at a fourth time point a fourth image is obtained, the third and fourth images being different from one another in view of the flowing contrast agent. A first time interpolation is performed for at least the first and second images at an intermediate time point between the first and second time points, and at least a second time interpolation is performed for the third and fourth images at an intermediate time point between the third and fourth time points. Using at least the first and second time interpolations, a reconstructed image is created.

DESCRIPTION OF THE PREFERRED EMBODIMENT

Figure 1:
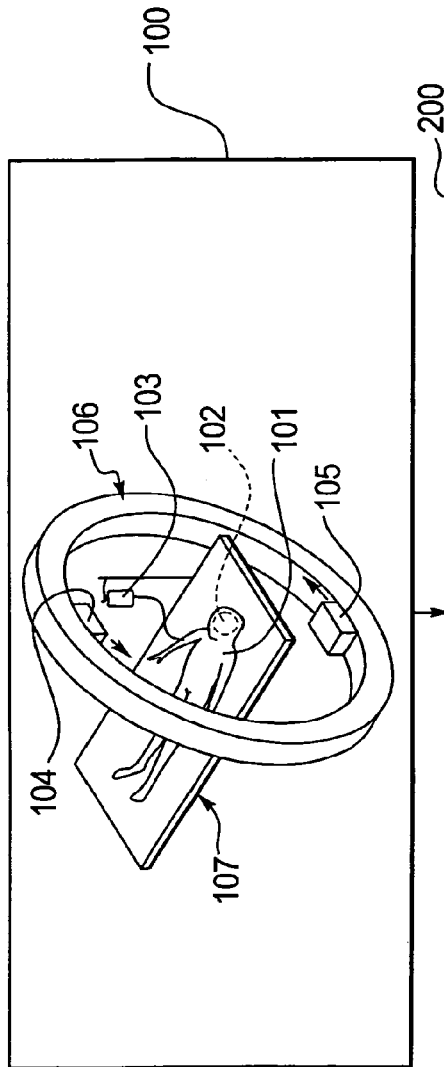
FIG. 1 is a block diagram showing method steps of a method for dynamic computed tomography of the preferred embodiment.

For the purposes of promoting an understanding of the principles of the invention, reference will now be made to the preferred embodiment illustrated in the drawings and specific language will be used to describe the same. It will nevertheless be understood that no limitation of the scope of the invention is thereby intended, such alterations and further modifications in the illustrated device, and/or method, and such further applications of the principles of the invention as illustrated therein being contemplated as would normally occur now or in the future to one skilled in the art to which the invention relates.

I. Overview

In the preferred embodiment discussed herein, the dynamic nature of the object is considered in the reconstruction step by associating to each projection image the time instant at which it was acquired. This leads to a time series of projection data for each projection angle since several complete data sets are acquired during a certain time in a perfusion study. As long as the temporal sampling satisfies Shannon's sampling theorem, i.e. as long as the Nyquist frequency of the sampling is larger than the maximum frequency of the TAC, projection data at any time instant can be computed by interpolation. In particular, a complete set of projection data can be synthesized for the same time instant to assure data consistency in the reconstruction step. Any reconstruction method can be applied to the set of projection data. A realization of temporal interpolation is described in the framework of partial block backprojection (PBB).

PBB performs interpolation in reconstructed image space which is computationally more efficient than interpolation in projection image space. PBB was first formulated by P. Grangeat, A. Koenig, T. Rodet, and S. Bonnet, "Theoretical Framework for a Dynamic Cone-Beam Reconstruction Algorithm Based on a Dynamic Particle Model," Physics in Medicine and Biology, vol. 47, 2002, pp. 2611-2626, but linear regression techniques were applied instead of temporal interpolation.

Temporal interpolation overcomes the restrictions in the sampling rate in perfusion studies. In particular, a reduction of the sampling rate is possible which is highly beneficial to adapt the frequency response of the data acquisition process to the frequency spectrum of the TAC. This allows: (i) noise reduction since the high frequency band without object information is not sampled anymore; (ii) total ray dose reduction since less data is acquired; and (iii) a total field-of-view increase e.g. by acquiring data of alternating regions of interest.

The preferred embodiment can be summarized as follows. An increase of time resolution is achieved in dynamic CT by taking into account the dynamic nature of the object directly in the reconstruction process. In the preferred embodiment a theoretical analysis is presented of the time resolution in dynamic CT. Data sets acquired over several cycles are interpreted as samples of a continuous signal. The sampling rate is chosen based on the maximum frequency of the dynamic changes of the process to reconstruct under the constraint of the rotational speed of the source. This way, for fast processes, a high time resolution can be attained by taking up to two samples per full rotation. For slow processes the time interval between samples can be increased. This may lead to a dose reduction if the source is properly switched off in the meantime. Consequently data at any time instant can be computed by interpolation techniques. The time interpolation approach is based on partial block backprojections. P. Gangeat, A. Koenig, T. Rodet, and S. Bonnet, "Theoretical Framework for a Dynamic Cone-beam Reconstruction Algorithm Based on a Dynamic Particle Model," Physics in Medicine and Biology, vol. 47, no. 15, August 2002. The algorithm uses polynomial spline interpolation to compute the values between samples and can be adapted for both fast and slow processes.

The preferred embodiment focuses on dynamic changes of the attenuation coefficient typically caused by the propagation of contrast agents. It is assumed that neither motion nor deformation occur. Under this assumption, it is disclosed herein, based on sampling theory, that the dynamic reconstruction problem can be reduced to the estimation of a continuous signal from noisy samples. Finally the theoretical results are validated with numerical simulations.

II. The Method Steps of the Preferred Embodiment

FIG. 1 shows steps of the method for dynamic computed tomography according to the present preferred embodiment. A block 100 illustrates in perspective patient table 107 on which a patient 101 is reclined. The patient has a region 102 of interest for scanning. A contrast agent 103 is injected into the patient which flows to and through the region of interest 102. For the dynamic computed tomography, a computed tomography (CT) machine 106 is provided having a ray source 104 (such as x-ray) and a ray detector 105 which, in known fashion, rotates about the region of interest 102 of the patient 101.

Images are created by the CT machine 106 and associated software and workstation in the following manner.

Figure 1A:
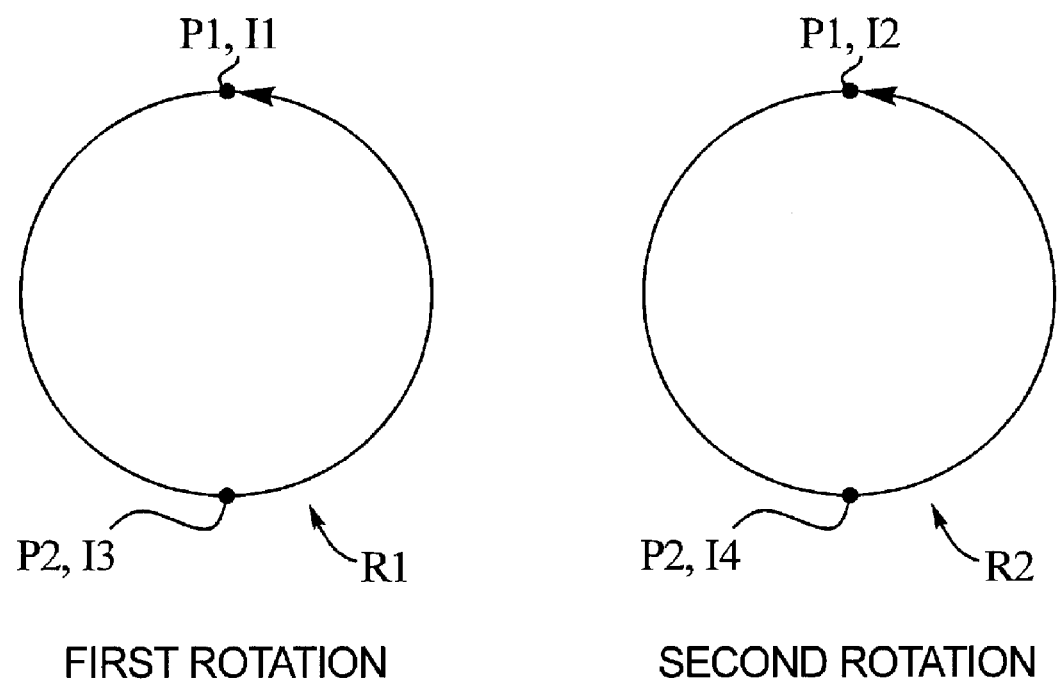
FIG. 1A shows rotational points at which images are acquired during the method of FIG.1.

As shown at block 200 and also in FIG. 1A, at a first rotational position P1 of the ray source for a first rotation R1 at a first time point a first image I1 is obtained, and at the first rotational position for another rotation R2 at a second time point a second image I2 is obtained, the first and second images I1 and I2 being different from one another in view of the flowing contrast agent. At another rotational position P2 of the ray source for the first rotation R1 at a third time point a third image I3 is obtained, and at the another rotational position R2 for the another rotation R2 at a fourth time point a fourth image I4 is obtained, the third and fourth images I3 and I4 being different from one another in view of the flowing contrast agent.

As shown at block 300, a first time interpolation is performed for at least the first and second images at an intermediate time point between the first and second time points, and at least a second time interpolation is performed for at least the third and fourth images at an intermediate time point between the third and fourth time points.

As shown at block 400, using at least the first and second time interpolations, a reconstructed image is created for the first and another rotations.

Only first and second rotational positions have been referred to. Of course there are many rotational positions such as 100 or more as the ray source rotates around the patient region of interest. Also, of course many rotations may occur in a typical scanning session such as 10 or more.

III. Dynamic Acquisition as Sampling

For the sake of simplicity the analyses are performed for one dimensional projections and sequences of 2D images.

Results are generalized for sequences of 3D images. The following conventions are used for time: upper case denotes time interval length whereas lower case indicates a time instant.

A. Sampling in Parallel Geometry

First consider a continuously rotating parallel-beam scanning scheme with its corresponding detector. The projection $P_\beta(u, t_\beta)$ is characterized by the projection $\beta \in [0, 2\pi]$ (angular position of a source at infinity), the Cartesian detector coordinate u and the time at which it is acquired $t_\beta = \omega/\beta$ (where $\omega$ is the rotational speed of the source).

In order to reconstruct an image frame at any time t one should know for each projection at projection angle $\beta$ its value at any time, i.e. one should know $P_\beta(u, t)$. In practice, however, the source turns with a finite rotational speed $\omega$. Thus, assuming the rotation starts at t=0 from $\beta=0$, the value of the projection corresponding to the angular position $\beta$ will only be known at $t_\beta$. After one half rotation of the source, the same projection will be acquired, but mirrored, at $t_\beta + T_\pi$. Thus what is acquired is, for each angular position $\beta$, a discrete sequence in time.

$$P_\beta^s(u,k) = P_\beta((-1)^k u, t_\beta + kT_\pi). \tag{1}$$

This dynamic acquisition process can be interpreted as the sampling of a dynamically changing projection $P_\beta(u, t)$ with a sampling period of $T_\pi$. In order to consider a more general case, one can take one sample every full-rotation or in general every m half-rotations. This can be of practical interest as the source could be switched off in the time interval between two samples, in this case (1) becomes $$P_\beta^s(u,k) = P_\beta((-1)^{km} u, t_\beta + kT_s) \tag{2}$$

where $T_\beta = mT_\pi$ is the temporal sampling interval. Note that in this case projections have only to be mirrored if m is odd.

According to Beer's law, a projection value is an accumulation of attenuation values. Thus the highest rate of change in the projection data will correspond to the highest rate of change of the attenuation values of the object. According to this one can apply Shannon's theorem (A. V. Oppenheim and R. W. Schafer, Discrete-Time Signal Processing. Prentice Hall, 1998).

If the time evolution of an object contains no frequencies higher than $v_{Nyq} = 1/(2T_s)$ (Nyquist frequency), all projection data at any time instance are completely determined by the series of samples obtained at discrete time instances taken in time intervals of length $T_s$.

Therefore given a maximum frequency $v_{max}$ for the dynamic changes in the object and a rotational speed of the source $\omega$, a value of m should be chosen such that $$m < \frac{\omega}{2\pi v_{max}} \tag{3}$$

That $$\frac{\omega}{2\pi v_{max}}$$

is bigger that 1 is ensured if the sampling condition given above is fulfilled. If the dynamic changes are slow enough, for a given rotational speed, several values of m will verify (3). However, for fast dynamic changes it might happen that $$1 < \frac{\omega}{2\pi v_{max}} < 2$$

and thus the only possible choice is m=1, i.e. to take two samples per full-rotation.

The value of the projections at any time can be computed as $$P_\beta(u, t) = \sum_{k \in Z} P_\beta^s(u, k)\psi(t - t_\beta - kT_s) \tag{4}$$

where $$\psi(t) = \mathrm{sinc}\left(\frac{t}{T_s}\right)$$

is the ideal interpolator. With the temporal interpolation of projection data a time series of reconstructed 2D images at any desired time instance can be obtained with any reconstruction algorithm for static objects.

Note that, in principle, this approach is valid for dynamic changes due both to time evolution and to motion or deformation. However, for the second case it is of no practical relevance since the displacement of non-smooth transitions in the image (e.g. between a high contrasted vessel and its surroundings) will cause very fast changes in the projections, causing the frequency spectrum of their temporal evolution to go beyond the Nyquist limit imposed by the highest possible sampling rate given a rotational speed of the scanner.

B. Sampling in Fan-Beam Geometry

Practical CT scanners acquire fan-beam projections. These are characterized by the angular position of the source $\alpha$, their fan angle $\gamma$ and the time at which they have been acquired $t_\alpha = \alpha/\omega$. The maximum fan-angle $2\gamma_{max}$ is determined by the size of the object. We have seen in the previous section that, for fast signals, it might only be possible to reconstruct the dynamic changes when taking two samples per full-rotation (m=1). For a parallel-beam projection $P_\beta(u, t)$, it suffices to mirror the projection to get the corresponding ray when m is odd. For fan-beam projections, however, if m is odd the projection at angular position $\alpha + m\pi$ will not be a mirrored version of the projection at $\alpha$ anymore. The ray $(\alpha, \gamma)$ (angular position of the source $\alpha$, fan-angular position of the ray $\gamma$), acquired at $t_\alpha$, is equivalent to the ray $(\alpha + \pi - \gamma, -\gamma)$ (conjugate rays), acquired at $t_\alpha + mT_\pi - T_\gamma$, where $T_\gamma = \gamma/w$. This implies a non-regular sampling scheme.

A simple way to avoid reconstruction from samples in a non-regular temporal grid is to rebin the fan-beam projections to parallel-beam ones. In the rebinned set of projections every ray in a projection will have been acquired at a different time instant. In an approximation; this is ignored by associating each projection to the time at which its central projection has been acquired. In this section an analysis is made of the error committed when ignoring the individual time of each ray in the rebinning step. A similar analysis can be found in S. Bonnet, A. Koenig, P. Hugonnard, and P. Grangeat, "Time Delay Analysis in Online 4-D CT," in Fully 3D Image Reconstruction Meeting in Radiology and Nuclear Medicine, 2003.

Figure 2:
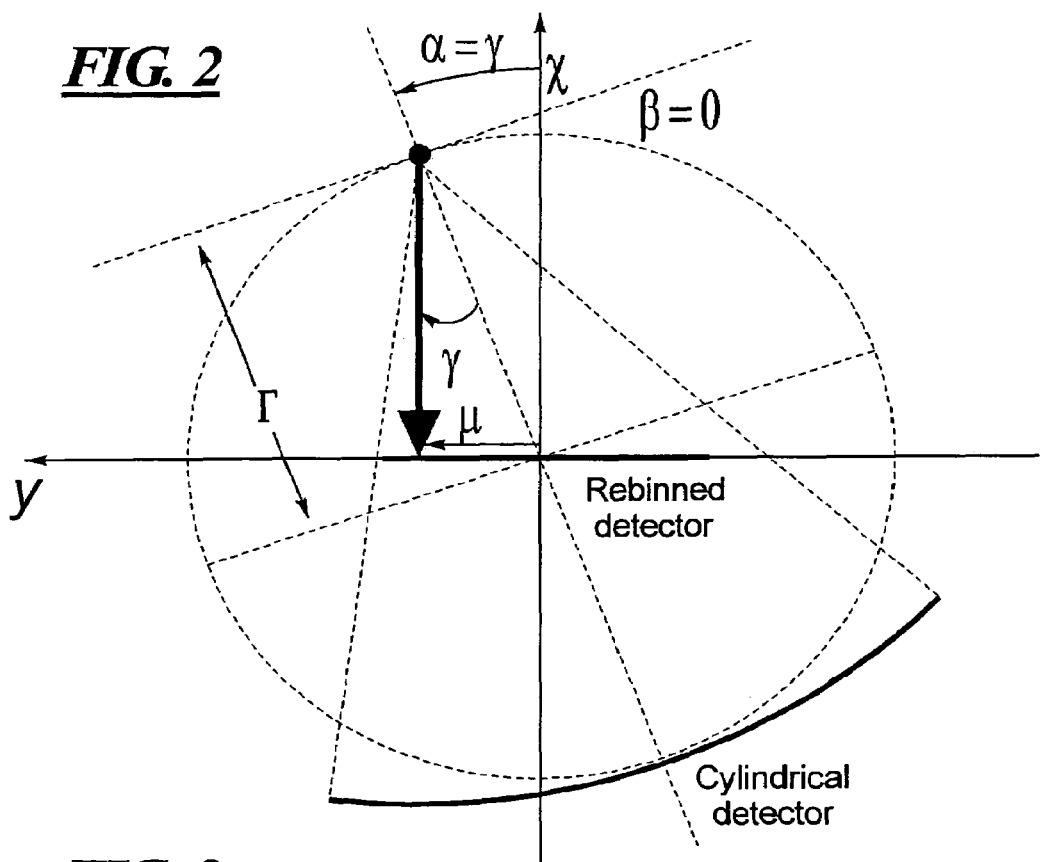
FIG. 2 is an illustration of a correspondence between fan-beam rays and parallel-beam rays on a virtual detector situated at an origin of coordinates in CT scanning.

Let one denote with $P_\alpha(\gamma, t_\alpha)$ the acquired fan-beam projections and with $$P_{\frac{r}{\beta}}(u, t_\beta(u))$$

the rebinned parallel-beam ones. Rebinning the fan-beam projections to parallel-beam ones can be expressed by the following, coordinate transform $$\gamma(u) \to \sin^-(u/\Gamma)$$

$$\alpha(\beta, u) \to \beta + \gamma(u) \quad (5)$$

where $\Gamma$ is the distance between source and origin. FIG. 2 shows equivalence between rays $$P_{\frac{r}{\beta}}(u) \text{ and } P_{\alpha(\beta,u)}(\gamma(u)) \text{ with } \gamma(u) = \sin^{-1}\left(\frac{u}{\Gamma}\right) \text{ and } \alpha(\beta, u) = \beta + \gamma(u).$$

Thus FIG. 2 illustrates the correspondence between fan-beam rays and parallel-beam rays on a virtual detector situated at the origin of coordinates. The maximum extension of the rebinned detector can be obtained from (5):

$$u_{max} = \Gamma \sin(\gamma_{max}). \quad (6)$$

IV. Filtered Backprojection as a Temporal Averaging Process

A. Parallel Geometry

The most widespread reconstruction algorithm in clinical applications of computed tomography is the filtered backprojection (FBP). Due to the linearity of the FBP the temporal interpolation can be performed both before or after the filtering and backprojecting every projection. Moreover, in an approximation one can accumulate the backprojected projections on an angular interval before performing the temporal interpolation step, so that at the end the number of interpolations is reduced. The question is, given a maximum frequency $v_{max}$ for the dynamic changes of the object, how wide can the angular interval be from which one can accumulate backprojected projections in order not to lose any significant information about time evolution?

Consider angular intervals of width $2\Pi/N$. The accumulation of the backprojected projections corresponding to each of these intervals is denoted by partial block backprojection (PBB). One can associate to the ith PBB the time at which the central projection of the ith angular interval is acquired, i.e.

$$t\frac{\pi}{N}(2i + 1).$$

The PBB for the ith interval evaluated at $x_0$ is $$PBB^i\left(x_0, t_{\frac{\pi}{N}(2i+1)}\right) = \frac{1}{2}\int_{\frac{2\pi}{N}i}^{\frac{2\pi}{N}(i+1)} \int_{-u_{max}}^{+u_{max}} \quad (7)$$
$$P_\beta(u, t_\beta)h(u_0(\beta) - u)\,du\,d\beta$$
$$= \frac{h(0)}{2}\int_{\frac{2\pi}{N}i}^{\frac{2\pi}{N}(i+1)} c(\beta/\omega)\,d\beta.$$

Once one has chosen an appropriate value of N, the temporal averaging effect of the accumulation of filtered backprojections from an angular interval is negligible. One can then perform the interpolation step on the PBBs. This way one can compute the value of each PBB at any instant t, $PBB_t(x, t)$. The final image can be obtained as $$FBP(x, t) = \sum_{i=0}^{N/2-1} PBB^i(x, t). \quad (8)$$

Note that (8) corresponds to a reconstruction with projections from a half-rotation (short-scan). A reconstruction with projections from a full-rotation (full-scan). A reconstruction with projections from a full-rotation (full-scan) is also possible as long as m>1 (less than two samples per full-rotation).

Note that not all combinations of m and N are possible. If m=1, for example, one needs two samples per full-rotation so that for each angular interval I there must be a corresponding angular interval i+N/2 within the full-rotation, that is: N must be even. The possible choices for m and N depend on $v_{max}$ and on the reconstruction mode desired (short-scan/full-scan). Switching off the source between two samples can have an influence as well.

B. Fan-Beam Geometry

In this section the temporal averaging effect of the PBB is analyzed within the framework of Rebinning fan-beam projections to parallel-beam projections. Note that in fan-beam projections for odd values of m angular intervals separated by $m\pi$ do not contain the same rays anymore so that there is no possibility to use an irregular sampling scheme as when considering individual projections. Therefore rebinning is the only possible alternative.

V. Temporal Interpolation

In the previous sections it has been shown that the problem of reconstructing a sequence of 2D frames from projections of a dynamically changing object can be reduced to an interpolation of a continuous signal from its samples and a CT static reconstruction. The temporal samples can be projection values or pixel values of PBBs. In the extreme case, if the dynamic changes are slow enough, the angular intervals of the PBB become the full angular range and therefore the samples become fully reconstructed 2D frames themselves.

The immediate question now is how does one perform the interpolation. In section I-A it has been affirmed that the reconstruction from samples verifying the Nyquist condition results from interpolating with an ideal interpolator. The ideal interpolator is an ideal low-pass filter, i.e. for a given sampling rate $1/T_s$ its frequency response is constant equal to $$T_s \text{ for } |v| < vN_{yq} = \frac{1}{2T_s}$$

and zero otherwise. The ideal interpolator has an infinite support and decays very slowly ($\alpha 1/|t|$) so that samples that lie far from the position of the point to interpolate will still make a significant contribution to its value. This makes it very inefficient for practical purposes.

An efficient interpolation scheme should have a frequency response close to the ideal low-pass filter and be nevertheless well localized around the point to interpolate. Polynomial splines have been shown to be a very good compromise M.

Figure 3:
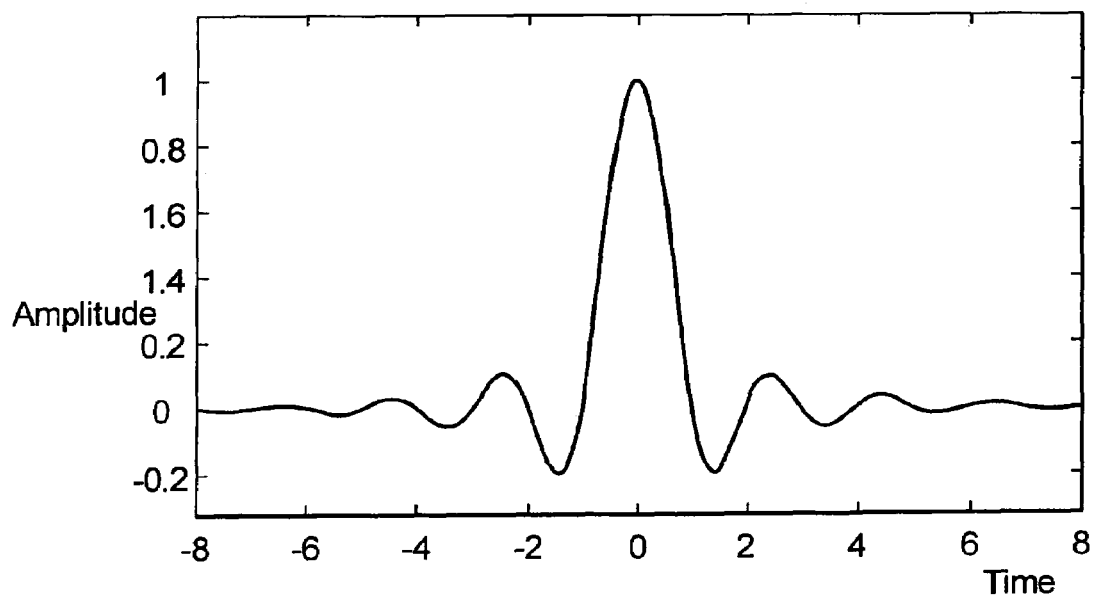
FIG. 3 is a graph showing amplitude versus time for both a polynomial spline interpolator of ninth order and an ideal interpolator.
Figure 4:
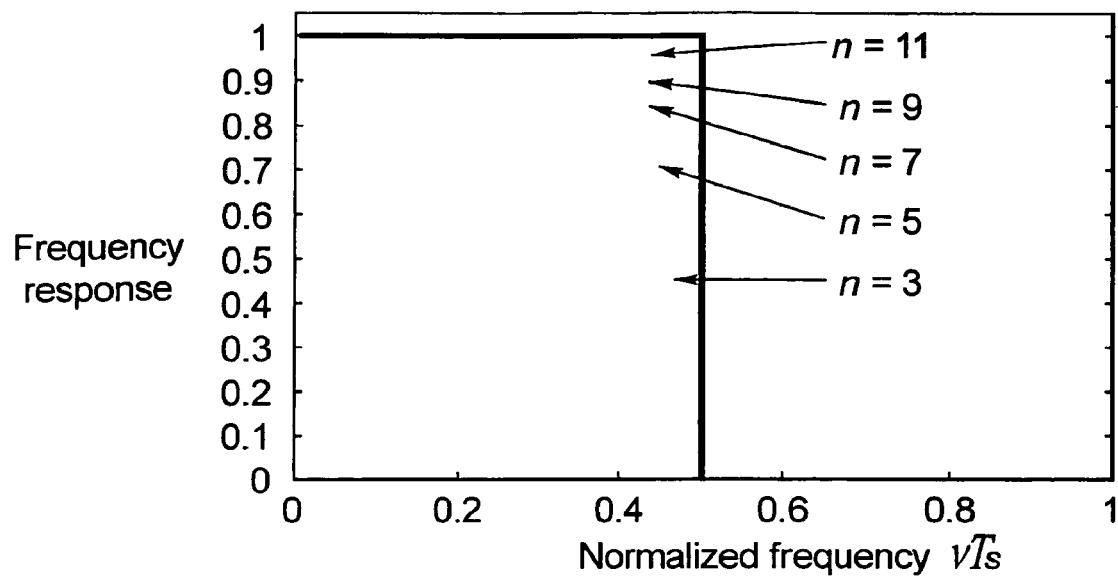
FIG. 4 shows a Fourier transform of a polynomial spline interpolator for different orders n.

Unser, "Splines—A Perfect Fit for Signal and Image Processing," IEEE Signal Processing Magazine, vol. 16, pp. 22-38, November 1999. The nth polynomial spline interpolator is a piece-wise polynomial of order n. A polynomial is fitted in every interval between two samples in such a way that the connection with the polynomial in the next interval is smooth and that it vanishes at the boundary of the interval. The resulting function is n−1 times differentiable at the connecting points. FIG. 3 shows a polynomial spline interpolator for n=9. Thus FIG. 3 shows both the polynomial spline interpolator of ninth order and the ideal interpolator. Inspite of the high order, the polynomial spline interpolator decays much faster than the ideal interpolator. On the other hand, FIG. 4 shows a Fourier transform of the polynomial spline interpolator for different orders n; and thus shows how the frequency response of the polynomial spline interpolator approaches the one of the ideal interpolator as n increases. It has been proven that the polynomial spline interpolator converges to the ideal interpolator when n→∞—See M. Unser article above. The convergence is very fast for the lower degrees. Convergence to the ideal interpolator is a very comfortable property for purposes since one can use n as a parameter that controls how close herein one is from the ideal interpolation. Finally polynomial splines have the advantage that they can be very efficiently implemented when the samples are equally spaced. M. Unser, A. Aldroubi, and M. Eden, "B-spline Signal Processing Part II-Efficient Design and Applications," IEEE Transactions on Signal Processing, vol. 41, no. 2, pp. 834-848, February 1993.

VI. The Algorithm

So far the entire analysis has been carried out for one dimensional projection data and 2D reconstruction with the filtered backprojection algorithm. The results can be straightforward generalized to 2D projections both for parallel beam geometry as for cone-beam geometry. For the parallel geometry case this is obvious. For the cone-beam case, cone-beam projections are rebinned to fan-parallel beam ones as described in H. Turbell, "Cone-beam Reconstruction Using Filtered Backprojection," Ph.D. dissertation, Department of Electrical Engineering, Linköping. In this case the time delay depends only on the horizontal coordinate of the detector and therefore the time dependency is as in the fan-beam case.

For the reconstruction, a cone-beam reconstruction algorithm for circular trajectories such as Feldkamp L. A. Feldkamp, L. C. Davis, and J. W. Kress, "Practical Cone-beam Algorithm," Journal of the Optical Society of America, vol. 1, no. 6, pp. 612-619, June 1984. can be used. The PBB is now the accumulation of filtered backprojected 2D projections over an angular interval of width $2\pi/N$.

A time interpolation approach is described herein that serves as a general framework for dynamic CT reconstruction for objects With time dependent attenuation coefficient. The algorithm has the following parameters:

m: sampling interval $T_s = mT\pi$

N: width of the angular interval $2\pi/N$.

n: order of the polynomial spline interpolation.

$T_{Tot}$: total acquisition time.

Mode: short-scan or full-scan reconstruction.

Figure 5:
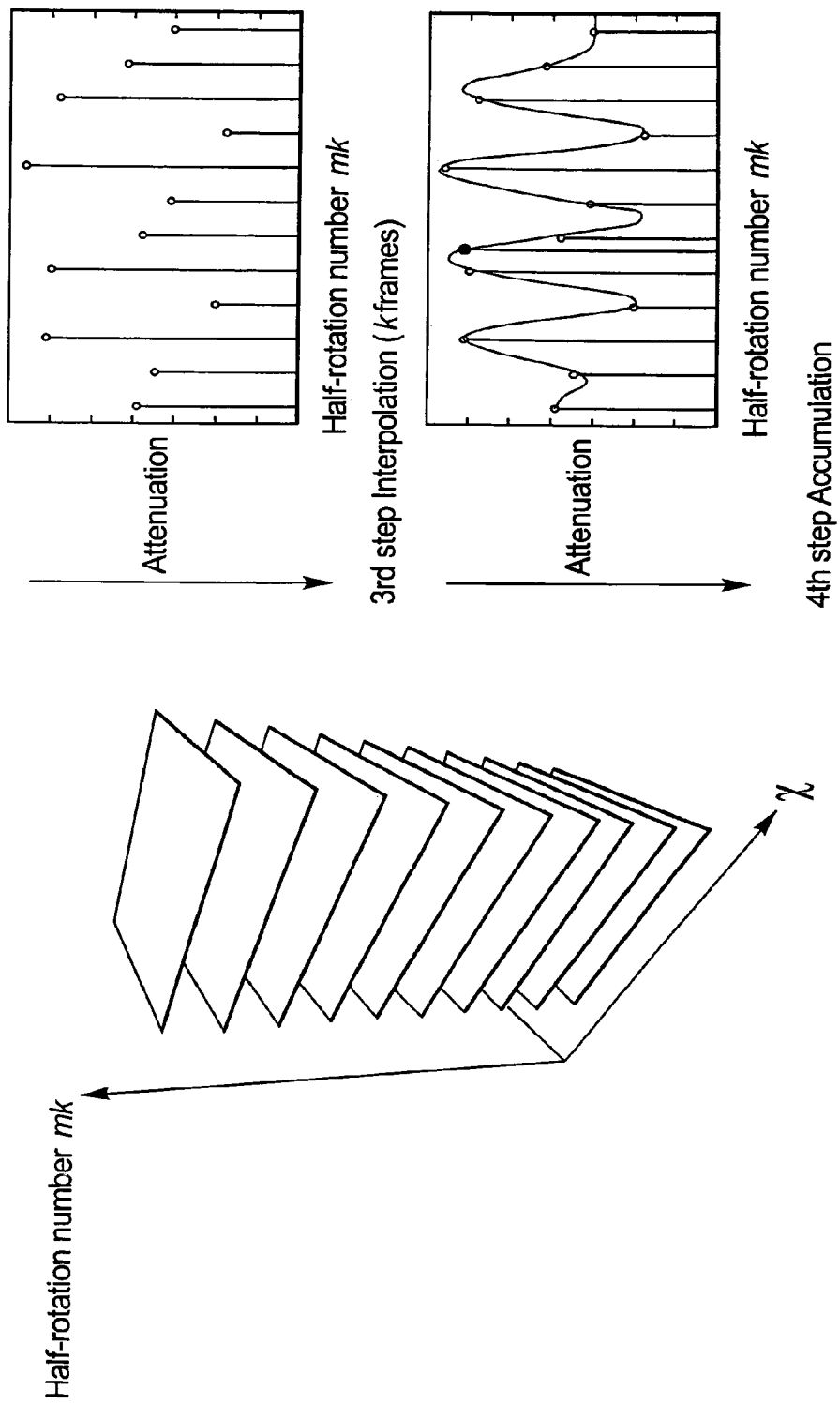
FIG. 5 shows a scheme for an interpolation approach according to the preferred embodiment.

The algorithm is described graphically in FIG. 5 which shows a scheme for the time interpolation approach, and comprises the following steps:

1st—Interval reconstruction:

Reconstruction of the necessary PBBs from the acquired projections using the T-FDK algorithm by M. Grass, T. Köhler, and R. Proksa, "3D Cone-beam CT Reconstruction for Circular Trajectories," Physics in Medicine and Biology, vol. 45, pp. 329-347, 2000.

2nd—Extraction of the samples:

For every pixel, extract and combine the samples of the corresponding PBBs.

If m is even extract the value of the ith PBB every m half rotations.

If m is odd extract the value of the ith and I+N/2th PBB every m half-rotations and combine them to a single signal.

3rd—Interpolation:

Interpolate the desired number of frames per full-turn using polynomial spline interpolation of degree n.

4th—Accumulation:

For each frame to reconstruct at time $t_i$, accumulate N/2 interpolated PBBs for a short-scan reconstruction (N PBBs for full-scan).

Some observations on the algorithm:

In case m is to be even other cone-beam reconstruction algorithms on circular trajectories can be used. E.g. C-FDK as described in H. Turbell above.

For each voxel of each PBB we have $K=T_{Tot}/(mT_\pi)$ samples. Depending on the mode, there is for each sample position k, N/2 (short-scan) or N (full-scan) PBBs. The reconstruction of N/2 (N) PBBs is equivalent to a short-scan (full-scan) cone-beam reconstruction from the computational cost point of view. The computational cost for the interpolation step is negligible compared to the cone-beam reconstruction. Therefore the total computational cost of the dynamic reconstruction of the sequence is equivalent to the cone-beam reconstruction of K image frames independently of the number of frames reconstructed.

VII. Temporal Estimation of Quasi Band-Limited Signals

The basic idea is now to better adapt the frequency response of the temporal estimation to the frequency band where the signal to reconstruct has significant frequency components. This will result in a ore efficient use of the acquired data that would allow to reduce the applied dose without any significant loss of quality in the reconstructed images. Two different approaches are provided.

A. Temporal Interpolation Approach

Figure 6:
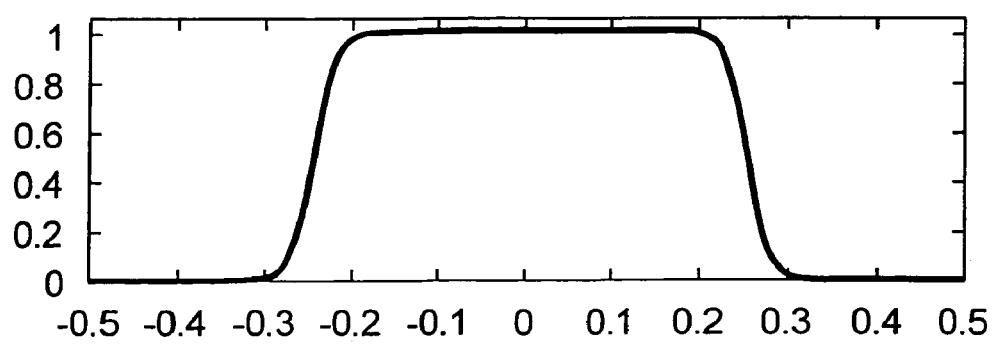
FIG. 6 shows a Fourier transform of a representative time attenuation curve.

The first approach is to adapt the Nyquist frequency to the frequency content of the signal. This is achieved e.g. by increasing the rotation time. This way the sampling period is larger and the periodic repetitions of the spectrum of the signal closer, see FIG. 6. FIG. 6 illustrates a Fourier transform of a representative time attenuation curve following a gamma-variate like temporal law (gray). The signal is sampled every $T_s=2$ sec with a rotation time of $T_{2\pi}=4$ sec. The black curve is the frequency response of the polynomial spline interpolator of order n=9.

As the spectrum now fills the Nyquist band using a nearest neighbor interpolation would result in the attenuation of significant frequency components. The time interpolation approach, based on polynomial splines interpolation, (See M. Unser, "Splines—A Perfect Fit for Signal and Image Processing," IEEE Signal Processing Magazine, vol. 16, pp. 22-38, November 1999.) presented in P. Montes and G. Lauritsch, "Analysis of Time Resolution in Dynamic Computed Tomography for Perfusion Studies," in 2004 IEEE Nuclear Science Symposium Conference Record, Rome, Italy, October 2004) preserves the signal. By keeping the dose per rotation, projections have the same signal to noise ratio as in the standard acquisition. Furthermore the interpolation approach has been shown not to increase the noise level (See P. Montes, above). Therefore the reconstructed frames should have the same noise level as in the standard reconstruction but the total dose would be reduced as less rotations are performed.

VIII. Outlook

An application for the time interpolation approach is the dynamic reconstruction of brain perfusion sequences. Since the bolus goes first through the lungs before it reaches the brain the temporal evolution of the attenuation coefficient is, in general, slow with respect to actual scanner rotational speeds. By using the time interpolation approach it is possible to reconstruct a dynamic sequence with less acquired data.

IX. Conclusions

Dynamic acquisition in CT can be modeled as a sampling process. By characterizing the dynamic changes of the object by their maximum frequency $v_{max}$ the minimum necessary sampling rate $1/T_s$ can be determined. The temporal distance between two samples $T_s$ is a multiple of the half-rotation time, $T_s = mT_\pi$. Intermediate values can be computed by interpolation. If $v_{max}$ is low relative to the rotational speed of the source, the interpolation can be performed on partial block backprojections (PBB) without losing any significant information about the dynamic changes of the object. It has been shown that a PBB has a temporal averaging effect and that this can be neglected if the width of its corresponding angular interval $2\pi/N$ is small enough. For cone-beam projections it has been shown that the same principles can be applied by rebinning the projections to a fan-parallel beam.

A time interpolation approach has been described that serves as a general framework for dynamic reconstruction, since it can be adapted for slower and faster processes. Given a $v_{max}$ and a rotational speed of the scanner $\omega$ one can choose a sampling rate $1/T_s$ with $T_s = mT_\pi$ such that $$m < \frac{\omega}{2\pi v_{max}}.$$

The algorithm performs then temporal interpolation on PBBs of width $2\pi/N$ using polynomial spline interpolation of order n.

The proposed approach can be used as well for slow dynamic processes. In this case, one can take a higher value of m, i.e. lower sampling rate, and let the interpolation compute the rest. The advantage of this is twofold. First, as less data are needed, dose can be reduced by properly switching off the source between two samples. Second it is computationally more efficient since only the equivalent of $K = T_{Tot}/T_s$ cone-beam reconstructions must be performed independently from the number of frames of the final sequence. In the extreme, for low $v_{max}$ relative to $\omega$, the interpolation can be performed in reconstructed image frames and the rest of the frames to complete the dynamic sequence can be computed by interpolation.

Herein, cone-beam reconstruction algorithms based on filtered backprojection have been described. Nevertheless the analysis in Section I is valid for any CT reconstruction method for circular trajectories since one only computes missing projection information by proper temporal interpolation. Even more, the approach can be easily generalized to any periodical trajectory.

Finally it should be pointed out that the proposed algorithm can be easily used in combination with a motion/deformation correction algorithm. Indeed it suffices to take into account the displacement vectors when extracting the samples of the PBBs (second step). In the more simple case of movement of a rigid body, which typically occurs in brain perfusion studies, it is enough to align the image frames using registration before applying the disclosed temporal interpolation approach.

While a preferred embodiment has been illustrated and described in detail in the drawings and foregoing description, the same is to be considered as illustrative and not restrictive in character, it being understood that only the preferred embodiment has been shown and described and that all changes and modifications that come within the spirit of the invention both now or in the future are desired to be protected.

We claim as our invention:

1. A method for dynamic computed tomography wherein a contrast agent is injected into a patient, and a region of interest of the patient where the contrast agent is flowing is then scanned with a computed tomography machine, the computed tomography machine having a ray source and a ray detector, at least the ray source rotating relative to said region of interest of the patient, comprising the steps of:
   at a first rotational position of the ray source for a first rotation at a first time point a first image is obtained, and at said first rotational position for at least another rotation at a second time point a second image is obtained, the first and second images being different from one another in view of the flowing contrast agent;
   for at least another rotational position of the ray source for said first rotation at a third time point a third image is obtained, and at said another rotational position for said another rotation at a fourth time point a fourth image is obtained, the third and fourth images being different from one another in view of the flowing contrast agent;
   performing a first time interpolation for at least said first and second images at an intermediate time point between said first and second time points, and performing at least a second time interpolation for at least said third and fourth images at an intermediate time point between said third and fourth time points;
   using at least said first and second time interpolations, creating a reconstructed image for said first and another rotations;
   wherein a sampling rate for the images obtained is chosen based on a maximum frequency of dynamic changes for the reconstructed image caused by the flowing of the contrast agent under constraint of a rotational speed of the ray source; and
   said ray source producing a fan beam and the temporal interpolation being performed between different beams of the fan beam.

2. A method of claim 1 wherein said intermediate time points for the first and second interpolations are the same.

3. A method of claim 1 wherein for each rotation there are at least 100 of said rotational positions.

4. A method of claim 1 wherein there are at least 10 of said rotations.

5. A method of claim 1 wherein said first and second time interpolations comprise a spline interpolation.

6. A method of claim 5 wherein the spline interpolation comprises a polynomial spline interpolation.

7. A method of claim 1 wherein rays of the fan beam are rebinned to parallel rays.

8. A method of claim 1 wherein said ray source comprises an x-ray source.

9. A method of claim 1 wherein the temporal interpolations are realized by use of partial block backprojection.

10. A method of claim 1 wherein the images obtained comprise a temporal image sampling which satisfies Shannon's sampling theorem wherein a Nyquist frequency of the sampling is larger than a maximum frequency of time attenuation curves.

11. A method of claim 1 wherein the images are obtained for a period of time of up to 40 seconds.

12. A method of claim 1 wherein a time period of each rotation of the ray source is approximately 1 second.

13. A method of clam 1 wherein each rotational position comprises a projection angle and said images obtained comprise projection images for each such projection angle, and more than two of said projection images are obtained for each angle, resulting in a time series of projection data for each projection angle.

14. A method of claim 1 wherein dynamic changes of attenuation coefficient caused by propagation of the contrast agent are taken into account by the method.

* * * * *